(12) United States Patent
Turner, Jr. et al.

(10) Patent No.: US 6,586,582 B2
(45) Date of Patent: Jul. 1, 2003

(54) HUMAN GABA RECEPTOR PROTEINS AND POLYNUCLEOTIDES ENCODING THE SAME

(75) Inventors: C. Alexander Turner, Jr., The Woodlands, TX (US); Brian Mathur, The Woodlands, TX (US); Glenn Friedrich, Houston, TX (US); Brian Zambrowicz, The Woodlands, TX (US); Arthur T. Sands, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 09/765,069

(22) Filed: Jan. 18, 2001

(65) Prior Publication Data

US 2002/0183507 A1 Dec. 5, 2002

Related U.S. Application Data

(60) Provisional application No. 60/176,692, filed on Jan. 18, 2000.

(51) Int. Cl.$^7$ .......................... C07K 1/00; C07H 21/04; C12N 1/20; C12P 21/06; G01N 33/566

(52) U.S. Cl. .......................... 536/23.5; 435/6; 435/7.1; 435/7.21; 435/69.5; 435/252.3; 435/320.1; 530/350; 436/501; 514/2

(58) Field of Search ........................ 536/23.5; 435/6, 435/7.1, 7.21, 69.5, 252.3, 380.1; 530/350; 436/501; 514/2

(56) References Cited

U.S. PATENT DOCUMENTS

| | | |
|---|---|---|
| 4,215,051 A | 7/1980 | Schroeder et al. |
| 4,631,211 A | 12/1986 | Houghten |
| 4,689,405 A | 8/1987 | Frank et al. |
| 4,713,326 A | 12/1987 | Dattagupta et al. |
| 4,946,778 A | 8/1990 | Ladner et al. |
| 5,252,743 A | 10/1993 | Barrett et al. |
| 5,424,186 A | 6/1995 | Fodor et al. |
| 5,445,934 A | 8/1995 | Fodor et al. |
| 5,556,752 A | 9/1996 | Lockhart et al. |
| 5,700,637 A | 12/1997 | Southern |
| 5,744,305 A | 4/1998 | Fodor et al. |
| 5,869,336 A | 2/1999 | Meyer et al. |
| 6,075,181 A | 6/2000 | Kucherlapati et al. |
| 6,150,584 A | 11/2000 | Kucherlapati et al. |

OTHER PUBLICATIONS

Bailey et al., Bioch. Biophys. Acta 1447(307–312)1999.*
Ogurusu et al., Bioch. Biophys. Acta 1305(15–18)1996.*
Berger and Kimmel, Eds., Methods in Enzymology, 152(432–442)1987.*
Sambrook et al., Molecular Cloning, p. 11.47, 1989.*
Bowie et al., 1990, Science 247:1306–1310, especially p.1306.*
Alexander et al., Proc. Natl. Acad. Sci. 89(3352–3356)1992.*
Bailey, Mark E.S., et al., "Genetic linkage and radiation hybrid mapping of the three human $GABA_c$ receptor ρ subunit genes: *GABRR1, GABRR2 and GABRR3*," *Biochimica et Biophysica Acta*, vol. 1447, No. 2–3, Oct. 28, 1999, pp. 307–312, XP000999020.
Ogurusu, Tarou, et al., "Cloning of a putative γ–aminobutyric acid (GABA) receptor subunit ρ3 cDNA," *Biochimica et Biophysica Acta*, vol. 1305, No. 1–2, Feb. 7, 1996, pp. 15–18, XP000999706.
Qian, Haohua, et al. "Molecular and Pharmacological Properties of GABA–ρ subunits from White Perch Retina," *J. Neurobiol.*, vol. 37, No. 2, 1998, pp. 305–320, XP000996647.
Cutting, Garry R., et al., "Cloning of the γ–aminobutyric acid (GABA) ρ1 cDNA: A GABA receptor subunit highly expressed in the retina," *Proc. Natl. Acad. Sci. USA.* vol. 88, Apr. 1991, pp. 2673–2677, XP002167521.
Cutting, Garry R. et al., "Identification of a Punative γ–aminobutyric acid (GABA) receptor $rho_2$ cDNA and colocalization of the genes encoding $rho^2$ (GABRR2) and $rho_1$ (GABRR1) to human chromosome 6q14–q21 and mouse chromosome 4," *Genomics*, vol. 12, No. 4, Apr. 1992, pp. 801–806, XP00099703.
Wegelius, Katri, et al., "Distribution of GABA receptor ρsubunit Transcripts in the rat brain," *European Journal of Neuroscience*, vol. 10, Jan. 1998, pp. 350–357, XP000996648.
Bird et al, 1988, "Single–Chain Antigen–Binding Proteins", Science 242:423–426.
Bitter et al, 1987, "Expression and Secretion Vectors for Yeast", Methods in Enzymology 153:516–544.
Colbere–Garapin et al, 1981, "A New Dominant Hybrid Selective Marker for Higher Eukaryotic Cells", J. Mol. Biol. 150:1–14.
Gautier et al, 1987, "α–DNA IV:αanomeric and β–anomeric tetrahymidylates covalently linked to intercalating oxazolopyridocarbazole. Synthesis, physiochemical properties and poly (rA) binding", Nucleic Acids Research 15(16):6625–6641.
Greenspan et al, 1993, "Idiotypes: structure and immunogenicity", FASEB Journal 7:437–444.
Huse et al, 1989, "Generation of a Large Combinatorial Library of the immunoglobulin Repertoire in Phage Lambda", Science 246:1275–1281.
Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.

(List continued on next page.)

*Primary Examiner*—Yvonne Eyler
*Assistant Examiner*—Michael Brannock

(57) ABSTRACT

Novel human polynucleotide and polypeptide sequences are disclosed that can be used in therapeutic, diagnostic, and pharmacogenomic applications.

8 Claims, No Drawings

OTHER PUBLICATIONS

Inoue et al, 1987, "Sequence–dependent hydrolysis of RNA using modified oligonucleotide splints and R Nase H", FEBS Letters 215(2):327–330.

Inoue et al, 1987, "Synthesis and hybridization studies on two complementary nona(2'–O–methyl)ribonucleotides", Nucleic Acids Research 15(15):6131–6149.

Inouye & Inouye, 1985, "Up–promoter mutations in the lpp gene of *Escherichia coli*", Nucleic Acids Research 13(9):3101–3110.

Janknecht et al, 1991, "Rapid and efficient purification of native histidine–tagged protein expressed by recombinant vaccinia virus", PNAS 88:8972–8976.

Kohler & Milstein, 1975, "Continuous cultures of fused cells secreting antibody of predefined specificity", Nature 256:495–497.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the Autographa californica Nuclear Polyhedrosis Virus Genome: Deletion Mutations within the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1980, "Transformation of mammalian cells with an amplifiable dominant–acting gene", Proc. Natl. Acad. Sci. USA 77(6):3567–3570.

* cited by examiner

HUMAN GABA RECEPTOR PROTEINS AND POLYNUCLEOTIDES ENCODING THE SAME

The present application claims the benefit of U.S. Provisional Application No. 60/176,692 which was filed on Jan. 18, 2000 and is herein incorporated by reference in its entirety.

1. INTRODUCTION

The present invention relates to the discovery, identification, and characterization of novel human polynucleotides encoding proteins that share sequence similarity with animal gamma-amino butyric acid (GABA) receptor subunits. The invention encompasses the described polynucleotides, host cell expression systems, the encoded proteins, fusion proteins, polypeptides and peptides, antibodies to the encoded proteins and peptides, and genetically engineered animals that either lack or over express the disclosed sequences, antagonists and agonists of the proteins, and other compounds that modulate the expression or activity of the proteins encoded by the disclosed sequences that can be used for diagnosis, drug screening, clinical trial monitoring and the treatment of diseases and disorders.

2. BACKGROUND OF THE INVENTION

Membrane proteins play important roles as, inter alia, cell surface markers, receptors, and mediators of signal transduction. GABA receptors bind a potent inhibitory neurotransmitter and this interaction serves as a target for a variety of pharmaceutical agents such as benzodiazepines, barbiturates and alcohol.

3. SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with membrane receptors such as, but not limited to human and other mammalian GABA receptors.

The novel human nucleic acid sequences described herein, encode alternative proteins/open reading frames (ORFs) of 467, 392, 180, 420, 345, and 133 amino acids in length (see SEQ ID NOS: 2, 4, 6, 8, 10, and 12 respectively).

The invention also encompasses agonists and antagonists of the described NHPs, including small molecules, large molecules, mutant NHPs, or portions thereof that compete with native NHP, peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP sequences (e.g., expression constructs that place the described sequence under the control of a strong promoter system), and transgenic animals that express a NHP transgene, or "knock-outs" (which can be conditional) that do not express a functional NHP. A gene trapped murine ES cell line has been produced that knocks-out a murine ortholog of the described NHPs.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of the described NHP ORFs that encode the described NHP amino acid sequences.

5. DETAILED DESCRIPTION OF THE INVENTION

The NHPs, described for the first time herein, are novel proteins that are expressed in, inter alia, human cell lines, human testis, brain, adrenal gland cells, and gene trapped human cells.

The present invention encompasses the nucleotides presented in the Sequence Listing, host cells expressing such nucleotides, the expression products of such nucleotides, and: (a) nucleotides that encode mammalian homologs of the described sequences, including the specifically described NHPs, and the NHP products; (b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of an NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encodes a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat.

No. 5,837,458). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package (Madison, Wis.) using standard default settings).

The invention also includes nucleic acid molecules, preferably DNA molecules, that hybridize to, and are therefore the complements of, the described NHP nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–12 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–12, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–12 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–12.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–12 provides detailed information about transcriptional changes involved in a specific pathway, potentially leading to the identification of novel components or gene functions that manifest themselves as novel phenotypes.

Probes consisting of sequences first disclosed in SEQ ID NOS:1–12 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–12 can be utilized in microarrays or other assay formats, to screen collections of genetic material from patients who have a particular medical condition. These investigations can also be carried out using the sequences first disclosed in SEQ ID NOS:1–12 in silico and by comparing previously collected genetic databases and the disclosed sequences using computer software known to those in the art.

Thus the sequences first disclosed in SEQ ID NOS:1–12 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–12. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid obtained from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP sequence). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, vision disorders, high blood pressure, depression, infertility, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor.)

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of the NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for an NHP, but can also identify compounds that trigger NHP-mediated activities or pathways.

Finally, the NHP products can be used as therapeutics. For example, soluble derivatives such as NHP peptides/domains corresponding to the NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and the corresponding deduced amino acid sequences of the described NHPs are presented in the Sequence Listing. The NHP nucleotides were obtained from clustered human gene trapped sequences, ESTs, and cDNA isolated from a human testis cell library. The described sequences share structural similarity with GABA receptor proteins, and particularly rho 3 subunits of the GABA receptor.

5.2 NHPS and NHP Polypeptides

NHPs, polypeptides, peptide fragments, mutated, truncated, or deleted forms of the NHPs, and/or NHP fusion proteins can be prepared for a variety of uses. These uses include but are not limited to the generation of antibodies, as reagents in diagnostic assays, for the identification of other cellular gene products related to a NHP, as reagents in assays for screening for compounds that can be as pharmaceutical reagents useful in the therapeutic treatment of mental, biological, or medical disorders and diseases. Given the similarity information and expression data, the described NHPs can be targeted (by drugs, oligos, antibodies, etc.) in order to treat disease, or to therapeutically augment the efficacy of therapeutic agents.

The Sequence Listing discloses the amino acid sequences encoded by the described NHP sequences. The NHPs typically display initiator methionines in DNA sequence contexts consistent with a translation initiation site, and a signal sequence characteristic of membrane or secreted proteins.

The NHP amino acid sequences of the invention include the amino acid sequences presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, transport, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP peptide or polypeptide is thought to be membrane protein, the hydrophobic regions of the protein can be excised and the resulting soluble peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that can be used for purposes of the invention include but are not limited to microorganisms such as bacteria (e.g., E. coli, B. subtilis) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the E. coli expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. A NHP coding sequence may be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$. nitriloacetic acid-agarose columns and histidine-tagged proteins are selectively eluted with imidazole-containing buffers.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96).

Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also favored is the production of fully humanized monoclonal antibodies as described in U.S. Pat. No. 6,150,584 and respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP mediated pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising the nucleotide sequence of SEQ ID NO:1.

2. An isolated nucleic acid molecule comprising a nucleotide sequence that:
   (a) encodes the amino acid sequence shown in SEQ ID NO:2; and
   (b) hybridizes under highly stringent conditions including washing in 0.1×SSC/0.1% SDS at 68° C. to the nucleotide sequence of SEQ ID NO: 1 or the complement thereof.

3. An isolated nucleic acid molecule comprising a nucleotide sequence that encodes the amino acid sequence shown in SEQ ID NO: 2.

4. An isolated nucleic acid molecule comprising a nucleotide sequence that encodes the amino acid sequence shown in SEQ ID NO: 8.

5. An expression vector comprising a nucleic acid sequence encoding the amino acid sequence of SEQ ID NO: 2.

6. A cell comprising the expression vector of claim 5.

7. An expression vector comprising a nucleic acid sequence encoding the amino acid sequence of SEQ ID NO: 8.

8. A cell comprising the expression vector of claim 7.

* * * * *

SEQUENCE LISTING

<160> NUMBER OF SEQ ID NOS: 12

<210> SEQ ID NO 1
<211> LENGTH: 1404
<212> TYPE: DNA
<213> ORGANISM: Homo sapiens

<400> SEQUENCE: 1

| | | | | | |
|---|---|---|---|---|---|
| atggtcctgg | ctttccagtt | agtctccttc | acctacatct | ggatcatatt | gaaaccaaat | 60 |
| gtttgtgctg | cttctaacat | caagatgaca | caccagcggt | gctcctcttc | aatgaaacaa | 120 |
| acctgcaaac | aagaaactag | aatgaagaaa | gatgacagta | ccaaagcgcg | gcctcagaaa | 180 |
| tatgagcaac | ttctccatat | agaggacaac | gatttcgcaa | tgagacctgg | atttggaggg | 240 |

```
tctccagtgc cagtaggtat agatgtccat gttgaaagca ttgacagcat ttcagagact    300
aacatggact ttacaatgac tttttatctc aggcattact ggaaagacga gaggctctcc    360
tttcctagca cagcaaacaa aagcatgaca tttgatcata gattgaccag aaagatctgg    420
gtgcctgata tcttttttgt ccactctaaa agatccttca tccatgatac aactatggag    480
aatatcatgc tgcgcgtaca ccctgatgga aacgtcctcc taagtctcag gataacggtt    540
tcggccatgt gctttatgga tttcagcagg tttcctcttg acactcaaaa ttgttctctt    600
gaactggaaa gctatgccta caatgaggat gacctaatgc tatactggaa acacggaaac    660
aagtccttaa atactgaaga acatatgtcc ctttctcagt tcttcattga agacttcagt    720
gcatctagtg gattagcttt ctatagcagc acaggttggc acaataggct tttcatcaac    780
tttgtgctaa ggaggcatgt tttcttcttt gtgctgcaaa cctatttccc agccatattg    840
atggtgatgc tttcatgggt ttcattttgg attgaccgaa gagctgttcc tgcaagagtt    900
tccctgggaa tcaccacagt gctgaccatg tccacaatca tcactgctgt gagcgcctcc    960
atgccccagg tgtcctacct caaggctgtg atgtgtacc tgtgggtcag ctccctcttt    1020
gtgttcctgt cagtcattga gtatgcagct gtgaactacc tcaccacagt ggaagagcgg    1080
aaacaattca agaagacagg aaagatttct aggatgtaca atattgatgc agttcaagct    1140
atggcctttg atggttgtta ccatgacagc gagattgaca tggaccagac ttccctctct    1200
ctaaactcag aagacttcat gaagaaaaa tcgatatgca gccccagcac cgattcatct    1260
cggataaaga gaagaaaatc cctaggagga catgttggta gaatcattct ggaaaacaac    1320
catgtcattg acacctattc taggattta ttccccattg tgtatatttt atttaatttg    1380
ttttactggg gtgtatatgt atga                                            1404
```

<210> SEQ ID NO 2
<211> LENGTH: 467
<212> TYPE: PRT
<213> ORGANISM: Homo sapiens
<400> SEQUENCE: 2

```
Met Val Leu Ala Phe Gln Leu Val Ser Phe Thr Tyr Ile Trp Ile Ile
 1               5                  10                  15

Leu Lys Pro Asn Val Cys Ala Ala Ser Asn Ile Lys Met Thr His Gln
            20                  25                  30

Arg Cys Ser Ser Met Lys Gln Thr Cys Lys Gln Glu Thr Arg Met
        35                  40                  45

Lys Lys Asp Asp Ser Thr Lys Ala Arg Pro Gln Lys Tyr Glu Gln Leu
    50                  55                  60

Leu His Ile Glu Asp Asn Asp Phe Ala Met Arg Pro Gly Phe Gly Gly
65                  70                  75                  80

Ser Pro Val Pro Val Gly Ile Asp Val His Val Glu Ser Ile Asp Ser
                85                  90                  95

Ile Ser Glu Thr Asn Met Asp Thr Met Thr Phe Tyr Leu Arg His
            100                 105                 110

Tyr Trp Lys Asp Glu Arg Leu Ser Phe Pro Ser Thr Ala Asn Lys Ser
        115                 120                 125

Met Thr Phe Asp His Arg Leu Thr Arg Lys Ile Trp Val Pro Asp Ile
    130                 135                 140

Phe Phe Val His Ser Lys Arg Ser Phe Ile His Asp Thr Thr Met Glu
145                 150                 155                 160
```

-continued

```
Asn Ile Met Leu Arg Val His Pro Asp Gly Asn Val Leu Leu Ser Leu
                165                 170                 175

Arg Ile Thr Val Ser Ala Met Cys Phe Met Asp Phe Ser Arg Phe Pro
            180                 185                 190

Leu Asp Thr Gln Asn Cys Ser Leu Glu Leu Glu Ser Tyr Ala Tyr Asn
        195                 200                 205

Glu Asp Asp Leu Met Leu Tyr Trp Lys His Gly Asn Lys Ser Leu Asn
    210                 215                 220

Thr Glu Glu His Met Ser Leu Ser Gln Phe Phe Ile Glu Asp Phe Ser
225                 230                 235                 240

Ala Ser Ser Gly Leu Ala Phe Tyr Ser Ser Thr Gly Trp Tyr Asn Arg
                245                 250                 255

Leu Phe Ile Asn Phe Val Leu Arg Arg His Val Phe Phe Val Leu
            260                 265                 270

Gln Thr Tyr Phe Pro Ala Ile Leu Met Val Met Leu Ser Trp Val Ser
        275                 280                 285

Phe Trp Ile Asp Arg Arg Ala Val Pro Ala Arg Val Ser Leu Gly Ile
    290                 295                 300

Thr Thr Val Leu Thr Met Ser Thr Ile Ile Thr Ala Val Ser Ala Ser
305                 310                 315                 320

Met Pro Gln Val Ser Tyr Leu Lys Ala Val Asp Val Tyr Leu Trp Val
                325                 330                 335

Ser Ser Leu Phe Val Phe Leu Ser Val Ile Glu Tyr Ala Ala Val Asn
            340                 345                 350

Tyr Leu Thr Thr Val Glu Glu Arg Lys Gln Phe Lys Lys Thr Gly Lys
        355                 360                 365

Ile Ser Arg Met Tyr Asn Ile Asp Ala Val Gln Ala Met Ala Phe Asp
    370                 375                 380

Gly Cys Tyr His Asp Ser Glu Ile Asp Met Asp Gln Thr Ser Leu Ser
385                 390                 395                 400

Leu Asn Ser Glu Asp Phe Met Arg Arg Lys Ser Ile Cys Ser Pro Ser
                405                 410                 415

Thr Asp Ser Ser Arg Ile Lys Arg Arg Lys Ser Leu Gly Gly His Val
            420                 425                 430

Gly Arg Ile Ile Leu Glu Asn Asn His Val Ile Asp Thr Tyr Ser Arg
        435                 440                 445

Ile Leu Phe Pro Ile Val Tyr Ile Leu Phe Asn Leu Phe Tyr Trp Gly
    450                 455                 460

Val Tyr Val
465
```

<210> SEQ ID NO 3
<211> LENGTH: 1179
<212> TYPE: DNA
<213> ORGANISM: Homo sapiens

<400> SEQUENCE: 3

| | | |
|---|---|---|
| atggtcctgg ctttccagtt agtctccttc acctacatct ggatcatatt gaaaccaaat | 60 |
| gtttgtgctg cttctaacat caagatgaca caccagcggt gctcctcttc aatgaaacaa | 120 |
| acctgcaaac aagaaactag aatgaagaaa gatgacagta ccaaagcgcg gcctcagaaa | 180 |
| tatgagcaac ttctccatat agaggacaac gatttcgcaa tgagacctgg atttggaggg | 240 |
| tctccagtgc cagtaggtat agatgtccat gttgaaagca ttgacagcat ttcagagact | 300 |
| aacatggact ttacaatgac ttttttatctc aggcattact ggaaagacga gaggctctcc | 360 |

```
tttcctagca cagcaaacaa aagcatgaca tttgatcata gattgaccag aaagatctgg      420
gtgcctgata tcttttttgt ccactctaaa agatccttca tccatgatac aactatggag      480
aatatcatgc tgcgcgtaca ccctgatgga aacgtcctcc taagtctcag gataacggtt      540
tcggccatgt gctttatgga tttcagcagg tttcctcttg acactcaaaa ttgttctctt      600
gaactggaaa gctatgccta caatgaggat gacctaatgc tatactggaa acacggaaac      660
aagtccttaa atactgaaga acatatgtcc ctttctcagt tcttcattga agacttcagt      720
gcatctagtg gattagcttt ctatagcagc acaggttggt acaataggct tttcatcaac      780
tttgtgctaa ggaggcatgt tttcttcttt gtgctgcaaa cctatttccc agccatattg      840
atggtgatgc tttcatgggt ttcattttgg attgaccgaa gagctgttcc tgcaagagtt      900
tccctgggaa tcaccacagt gctgaccatg tccacaatca tcactgctgt gagcgcctcc      960
atgccccagg tgtcctacct caaggctgtg gatgtgtacc tgtgggtcag ctccctcttt     1020
gtgttcctgt cagtcattga gtatgcagct gtgaactacc tcaccacagt ggaagagcgg     1080
aaacaattca gaagacagg aaaggtacag ccttgctctg actatcagat cccttgggga     1140
atgtggaaaa gactacccctt atctattgcc ctctcttga                            1179
```

<210> SEQ ID NO 4
<211> LENGTH: 392
<212> TYPE: PRT
<213> ORGANISM: Homo sapiens

<400> SEQUENCE: 4

```
Met Val Leu Ala Phe Gln Leu Val Ser Phe Thr Tyr Ile Trp Ile Ile
  1               5                  10                  15

Leu Lys Pro Asn Val Cys Ala Ala Ser Asn Ile Lys Met Thr His Gln
             20                  25                  30

Arg Cys Ser Ser Met Lys Gln Thr Cys Lys Gln Glu Thr Arg Met
         35                  40                  45

Lys Lys Asp Asp Ser Thr Lys Ala Arg Pro Gln Lys Tyr Glu Gln Leu
     50                  55                  60

Leu His Ile Glu Asp Asn Asp Phe Ala Met Arg Pro Gly Phe Gly Gly
 65                  70                  75                  80

Ser Pro Val Pro Val Gly Ile Asp Val His Val Glu Ser Ile Asp Ser
                 85                  90                  95

Ile Ser Glu Thr Asn Met Asp Phe Thr Met Thr Phe Tyr Leu Arg His
            100                 105                 110

Tyr Trp Lys Asp Glu Arg Leu Ser Phe Pro Ser Thr Ala Asn Lys Ser
        115                 120                 125

Met Thr Phe Asp His Arg Leu Thr Arg Lys Ile Trp Val Pro Asp Ile
    130                 135                 140

Phe Phe Val His Ser Lys Arg Ser Phe Ile His Asp Thr Thr Met Glu
145                 150                 155                 160

Asn Ile Met Leu Arg Val His Pro Asp Gly Asn Val Leu Leu Ser Leu
                165                 170                 175

Arg Ile Thr Val Ser Ala Met Cys Phe Met Asp Phe Ser Arg Phe Pro
            180                 185                 190

Leu Asp Thr Gln Asn Cys Ser Leu Glu Leu Glu Ser Tyr Ala Tyr Asn
        195                 200                 205

Glu Asp Asp Leu Met Leu Tyr Trp Lys His Gly Asn Lys Ser Leu Asn
    210                 215                 220
```

| | | | | | | | | | | | | |
|---|---|---|---|---|---|---|---|---|---|---|---|---|
|Thr|Glu|Glu|His|Met|Ser|Leu|Ser|Gln|Phe|Phe|Ile|Glu|Asp|Phe|Ser|
|225| | | | |230| | | | |235| | | | |240|

Thr Glu Glu His Met Ser Leu Ser Gln Phe Phe Ile Glu Asp Phe Ser
225                 230                 235                 240

Ala Ser Ser Gly Leu Ala Phe Tyr Ser Thr Gly Trp Tyr Asn Arg
                245                 250                 255

Leu Phe Ile Asn Phe Val Leu Arg Arg His Val Phe Phe Val Leu
                260                 265                 270

Gln Thr Tyr Phe Pro Ala Ile Leu Met Val Met Leu Ser Trp Val Ser
            275                 280                 285

Phe Trp Ile Asp Arg Arg Ala Val Pro Ala Arg Val Ser Leu Gly Ile
    290                 295                 300

Thr Thr Val Leu Thr Met Ser Thr Ile Ile Thr Ala Val Ser Ala Ser
305                 310                 315                 320

Met Pro Gln Val Ser Tyr Leu Lys Ala Val Asp Val Tyr Leu Trp Val
                325                 330                 335

Ser Ser Leu Phe Val Phe Leu Ser Val Ile Glu Tyr Ala Ala Val Asn
            340                 345                 350

Tyr Leu Thr Thr Val Glu Glu Arg Lys Gln Phe Lys Lys Thr Gly Lys
            355                 360                 365

Val Gln Pro Cys Ser Asp Tyr Gln Ile Pro Trp Gly Met Trp Lys Arg
    370                 375                 380

Leu Pro Leu Ser Ile Ala Leu Ser
385                 390

<210> SEQ ID NO 5
<211> LENGTH: 543
<212> TYPE: DNA
<213> ORGANISM: Homo sapiens

<400> SEQUENCE: 5

```
atggtcctgg ctttccagtt agtctccttc acctacatct ggatcatatt gaaaccaaat      60
gtttgtgctg cttctaacat caagatgaca caccagcggt gctcctcttc aatgaaacaa     120
acctgcaaac aagaaactag aatgaagaaa gatgacagta ccaaagcgcg gcctcagaaa     180
tatgagcaac ttctccatat agaggacaac gatttcgcaa tgagacctgg atttggaggg     240
tctccagtgc cagtaggtat agatgtccat gttgaaagca ttgacagcat ttcagagact     300
aacatggact ttacaatgac tttttatctc aggcattact ggaaagacga gaggctctcc     360
tttcctagca cagcaaacaa aagcatgaca tttgatcata gattgaccag aaagatctgg     420
gtgcctgata tcttttttgt ccactctaaa agatccttca tccatgatac aactatggag     480
aatatcatgc tgcgcgtaca ccctgatgga aacgtcctcc taagtctcag atgcctacaa     540
tga                                                                   543
```

<210> SEQ ID NO 6
<211> LENGTH: 180
<212> TYPE: PRT
<213> ORGANISM: Homo sapiens

<400> SEQUENCE: 6

Met Val Leu Ala Phe Gln Leu Val Ser Phe Thr Tyr Ile Trp Ile Ile
1               5                   10                  15

Leu Lys Pro Asn Val Cys Ala Ala Ser Asn Ile Lys Met Thr His Gln
            20                  25                  30

Arg Cys Ser Ser Met Lys Gln Thr Cys Lys Gln Glu Thr Arg Met
        35                  40                  45

Lys Lys Asp Asp Ser Thr Lys Ala Arg Pro Gln Lys Tyr Glu Gln Leu

|   |   |   |   |   | 50  |   |   |   |   | 55  |   |   |   |   | 60  |   |   |
|---|---|---|---|---|-----|---|---|---|---|-----|---|---|---|---|-----|---|---|

Leu His Ile Glu Asp Asn Asp Phe Ala Met Arg Pro Gly Phe Gly Gly
65                  70                  75                  80

Ser Pro Val Pro Val Gly Ile Asp Val His Val Glu Ser Ile Asp Ser
                85                  90                  95

Ile Ser Glu Thr Asn Met Asp Phe Thr Met Thr Phe Tyr Leu Arg His
            100                 105                 110

Tyr Trp Lys Asp Glu Arg Leu Ser Phe Pro Ser Thr Ala Asn Lys Ser
        115                 120                 125

Met Thr Phe Asp His Arg Leu Thr Arg Lys Ile Trp Val Pro Asp Ile
    130                 135                 140

Phe Phe Val His Ser Lys Arg Ser Phe Ile His Asp Thr Thr Met Glu
145                 150                 155                 160

Asn Ile Met Leu Arg Val His Pro Asp Gly Asn Val Leu Leu Ser Leu
                165                 170                 175

Arg Cys Leu Gln
        180

<210> SEQ ID NO 7
<211> LENGTH: 1263
<212> TYPE: DNA
<213> ORGANISM: Homo sapiens

<400> SEQUENCE: 7

| atgaagaaag | atgacagtac | caaagcgcgg | cctcagaaat | atgagcaact | tctccatata |   60 |
| gaggacaacg | atttcgcaat | gagacctgga | tttggagggt | ctccagtgcc | agtaggtata |  120 |
| gatgtccatg | ttgaaagcat | tgacagcatt | tcagagacta | catggactt  | tacaatgact |  180 |
| ttttatctca | ggcattactg | gaaagacgag | aggctctcct | tcctagcac  | agcaaacaaa |  240 |
| agcatgacat | ttgatcatag | attgaccaga | aagatctggg | tgcctgatat | cttttttgtc |  300 |
| cactctaaaa | gatccttcat | ccatgataca | actatggaga | tatcatgct  | gcgcgtacac |  360 |
| cctgatggaa | acgtcctcct | aagtctcagg | ataacggttt | cggccatgtg | ctttatggat |  420 |
| ttcagcaggt | ttcctcttga | cactcaaaat | tgttctcttg | aactggaaag | ctatgcctac |  480 |
| aatgaggatg | acctaatgct | atactggaaa | cacggaaaca | agtccttaaa | tactgaagaa |  540 |
| catatgtccc | tttctcagtt | cttcattgaa | gacttcagtg | catctagtgg | attagctttc |  600 |
| tatagcagca | caggttggta | caataggctt | tcatcaact  | ttgtgctaag | gaggcatgtt |  660 |
| ttcttctttg | tgctgcaaac | ctatttccca | gccatattga | tggtgatgct | tcatgggtt  |  720 |
| tcattttgga | ttgaccgaag | agctgttcct | gcaagagttt | ccctgggaat | caccacagtg |  780 |
| ctgaccatgt | ccacaatcat | cactgctgtg | agcgcctcca | tgccccaggt | gtcctacctc |  840 |
| aaggctgtgg | atgtgtacct | gtgggtcagc | tccctctttg | tgttcctgtc | agtcattgag |  900 |
| tatgcagctg | tgaactacct | caccacagtg | gaagagcgga | acaattcaa  | gaagacagga |  960 |
| aagatttcta | ggatgtacaa | tattgatgca | gttcaagcta | tggcctttga | tggttgttac |  1020 |
| catgacagcg | agattgacat | ggaccagact | tccctctctc | taaactcaga | agacttcatg |  1080 |
| agaagaaaat | cgtatgcag  | ccccagcacc | gattcatctc | ggataaagag | aagaaaatcc |  1140 |
| ctaggaggac | atgttggtag | aatcattctg | gaaaacaacc | atgtcattga | cacctattct |  1200 |
| aggattttat | tccccattgt | gtatattttt | tttaatttgt | tttactgggg | tgtatatgta |  1260 |
| tga        |            |            |            |            |            | 1263 |

-continued

```
<210> SEQ ID NO 8
<211> LENGTH: 420
<212> TYPE: PRT
<213> ORGANISM: Homo sapiens

<400> SEQUENCE: 8

Met Lys Lys Asp Asp Ser Thr Lys Ala Arg Pro Gln Lys Tyr Glu Gln
  1               5                  10                  15

Leu Leu His Ile Glu Asp Asn Asp Phe Ala Met Arg Pro Gly Phe Gly
             20                  25                  30

Gly Ser Pro Val Pro Val Gly Ile Asp Val His Val Glu Ser Ile Asp
         35                  40                  45

Ser Ile Ser Glu Thr Asn Met Asp Phe Thr Met Thr Phe Tyr Leu Arg
 50                      55                  60

His Tyr Trp Lys Asp Glu Arg Leu Ser Phe Pro Ser Thr Ala Asn Lys
 65                  70                  75                  80

Ser Met Thr Phe Asp His Arg Leu Thr Arg Lys Ile Trp Val Pro Asp
                 85                  90                  95

Ile Phe Phe Val His Ser Lys Arg Ser Phe Ile His Asp Thr Thr Met
                100                 105                 110

Glu Asn Ile Met Leu Arg Val His Pro Asp Gly Asn Val Leu Leu Ser
            115                 120                 125

Leu Arg Ile Thr Val Ser Ala Met Cys Phe Met Asp Phe Ser Arg Phe
130                 135                 140

Pro Leu Asp Thr Gln Asn Cys Ser Leu Glu Leu Glu Ser Tyr Ala Tyr
145                 150                 155                 160

Asn Glu Asp Asp Leu Met Leu Tyr Trp Lys His Gly Asn Lys Ser Leu
                165                 170                 175

Asn Thr Glu Glu His Met Ser Leu Ser Gln Phe Phe Ile Glu Asp Phe
                180                 185                 190

Ser Ala Ser Ser Gly Leu Ala Phe Tyr Ser Ser Thr Gly Trp Tyr Asn
            195                 200                 205

Arg Leu Phe Ile Asn Phe Val Leu Arg Arg His Val Phe Phe Phe Val
        210                 215                 220

Leu Gln Thr Tyr Phe Pro Ala Ile Leu Met Val Met Leu Ser Trp Val
225                 230                 235                 240

Ser Phe Trp Ile Asp Arg Arg Ala Val Pro Ala Arg Val Ser Leu Gly
                245                 250                 255

Ile Thr Thr Val Leu Thr Met Ser Thr Ile Ile Thr Ala Val Ser Ala
                260                 265                 270

Ser Met Pro Gln Val Ser Tyr Leu Lys Ala Val Asp Val Tyr Leu Trp
            275                 280                 285

Val Ser Ser Leu Phe Val Phe Leu Ser Val Ile Glu Tyr Ala Ala Val
        290                 295                 300

Asn Tyr Leu Thr Thr Val Glu Glu Arg Lys Gln Phe Lys Lys Thr Gly
305                 310                 315                 320

Lys Ile Ser Arg Met Tyr Asn Ile Asp Ala Val Gln Ala Met Ala Phe
                325                 330                 335

Asp Gly Cys Tyr His Asp Ser Glu Ile Asp Met Asp Gln Thr Ser Leu
            340                 345                 350

Ser Leu Asn Ser Glu Asp Phe Met Arg Arg Lys Ser Ile Cys Ser Pro
        355                 360                 365

Ser Thr Asp Ser Ser Arg Ile Lys Arg Arg Lys Ser Leu Gly Gly His
370                 375                 380
```

Val Gly Arg Ile Ile Leu Glu Asn Asn His Val Ile Asp Thr Tyr Ser
385                 390                 395                 400

Arg Ile Leu Phe Pro Ile Val Tyr Ile Leu Phe Asn Leu Phe Tyr Trp
            405                 410                 415

Gly Val Tyr Val
            420

<210> SEQ ID NO 9
<211> LENGTH: 1038
<212> TYPE: DNA
<213> ORGANISM: Homo sapiens

<400> SEQUENCE: 9

```
atgaagaaag atgacagtac caaagcgcgg cctcagaaat atgagcaact tctccatata    60
gaggacaacg atttcgcaat gagacctgga tttggagggt ctccagtgcc agtaggtata   120
gatgtccatg ttgaaagcat tgacagcatt tcagagacta catggactt tacaatgact   180
ttttatctca ggcattactg gaaagacgag aggctctcct ttcctagcac agcaaacaaa   240
agcatgacat tgatcatag attgaccaga agatctgggt gcctgatat ctttttgtc    300
cactctaaaa gatccttcat ccatgataca actatggaga atatcatgct gcgcgtacac   360
cctgatggaa acgtcctcct aagtctcagg ataacggttt cggccatgtg ctttatggat   420
tcagcaggt ttcctcttga cactcaaaat tgttctcttg aactggaaag ctatgcctac   480
aatgaggatg acctaatgct atactggaaa cacggaaaca agtccttaaa tactgaagaa   540
catatgtccc tttctcagtt cttcattgaa gacttcagtg catctagtgg attagctttc   600
tatagcagca caggttggta caataggctt tcatcaact ttgtgctaag gaggcatgtt   660
ttcttctttg tgctgcaaac ctatttccca gccatattga tggtgatgct ttcatgggtt   720
tcattttgga ttgaccgaag agctgttcct gcaagagttt ccctgggaat caccacagtg   780
ctgaccatgt ccacaatcat cactgctgtg agcgcctcca tgccccaggt gtcctacctc   840
aaggctgtgg atgtgtacct gtgggtcagc tccctctttg tgttcctgtc agtcattgag   900
tatgcagctg tgaactacct caccacagtg gaagagcgga aacaattcaa gaagacagga   960
aaggtacagc cttgctctga ctatcagatc ccttggggaa tgtggaaaag actaccctta  1020
tctattgccc tctcttga                                                1038
```

<210> SEQ ID NO 10
<211> LENGTH: 345
<212> TYPE: PRT
<213> ORGANISM: Homo sapiens

<400> SEQUENCE: 10

Met Lys Lys Asp Asp Ser Thr Lys Ala Arg Pro Gln Lys Tyr Glu Gln
1               5                   10                  15

Leu Leu His Ile Glu Asp Asn Asp Phe Ala Met Arg Pro Gly Phe Gly
                20                  25                  30

Gly Ser Pro Val Pro Val Gly Ile Asp Val His Val Glu Ser Ile Asp
            35                  40                  45

Ser Ile Ser Glu Thr Asn Met Asp Phe Thr Met Thr Phe Tyr Leu Arg
        50                  55                  60

His Tyr Trp Lys Asp Glu Arg Leu Ser Phe Pro Ser Thr Ala Asn Lys
65                  70                  75                  80

Ser Met Thr Phe Asp His Arg Leu Thr Arg Lys Ile Trp Val Pro Asp
                85                  90                  95

-continued

```
Ile Phe Phe Val His Ser Lys Arg Ser Phe Ile His Asp Thr Thr Met
            100                 105                 110
Glu Asn Ile Met Leu Arg Val His Pro Asp Gly Asn Val Leu Leu Ser
        115                 120                 125
Leu Arg Ile Thr Val Ser Ala Met Cys Phe Met Asp Phe Ser Arg Phe
130                 135                 140
Pro Leu Asp Thr Gln Asn Cys Ser Leu Glu Leu Glu Ser Tyr Ala Tyr
145                 150                 155                 160
Asn Glu Asp Asp Leu Met Leu Tyr Trp Lys His Gly Asn Lys Ser Leu
                165                 170                 175
Asn Thr Glu Glu His Met Ser Leu Ser Gln Phe Phe Ile Glu Asp Phe
            180                 185                 190
Ser Ala Ser Ser Gly Leu Ala Phe Tyr Ser Ser Thr Gly Trp Tyr Asn
        195                 200                 205
Arg Leu Phe Ile Asn Phe Val Leu Arg Arg His Val Phe Phe Phe Val
    210                 215                 220
Leu Gln Thr Tyr Phe Pro Ala Ile Leu Met Val Met Leu Ser Trp Val
225                 230                 235                 240
Ser Phe Trp Ile Asp Arg Arg Ala Val Pro Ala Arg Val Ser Leu Gly
                245                 250                 255
Ile Thr Thr Val Leu Thr Met Ser Thr Ile Ile Thr Ala Val Ser Ala
            260                 265                 270
Ser Met Pro Gln Val Ser Tyr Leu Lys Ala Val Asp Val Tyr Leu Trp
        275                 280                 285
Val Ser Ser Leu Phe Val Phe Leu Ser Val Ile Glu Tyr Ala Ala Val
    290                 295                 300
Asn Tyr Leu Thr Thr Val Glu Glu Arg Lys Gln Phe Lys Lys Thr Gly
305                 310                 315                 320
Lys Val Gln Pro Cys Ser Asp Tyr Gln Ile Pro Trp Gly Met Trp Lys
                325                 330                 335
Arg Leu Pro Leu Ser Ile Ala Leu Ser
            340                 345
```

<210> SEQ ID NO 11
<211> LENGTH: 402
<212> TYPE: DNA
<213> ORGANISM: Homo sapiens

<400> SEQUENCE: 11

| | |
|---|---|
| atgaagaaag atgacagtac caaagcgcgg cctcagaaat atgagcaact tctccatata | 60 |
| gaggacaacg atttcgcaat gagacctgga tttggagggt ctccagtgcc agtaggtata | 120 |
| gatgtccatg ttgaaagcat tgacagcatt tcagagacta acatggactt tacaatgact | 180 |
| ttttatctca ggcattactg gaaagacgag aggctctcct ttcctagcac agcaaacaaa | 240 |
| agcatgacat ttgatcatag attgaccaga aagatctggg tgcctgatat cttttttgtc | 300 |
| cactctaaaa gatccttcat ccatgataca actatggaga atatcatgct gcgcgtacac | 360 |
| cctgatggaa acgtcctcct aagtctcaga tgcctacaat ga | 402 |

<210> SEQ ID NO 12
<211> LENGTH: 133
<212> TYPE: PRT
<213> ORGANISM: Homo sapiens

<400> SEQUENCE: 12

Met Lys Lys Asp Asp Ser Thr Lys Ala Arg Pro Gln Lys Tyr Glu Gln

-continued

```
1               5                    10                    15
Leu Leu His Ile Glu Asp Asn Asp Phe Ala Met Arg Pro Gly Phe Gly
            20                  25              30

Gly Ser Pro Val Pro Val Gly Ile Asp Val His Val Glu Ser Ile Asp
        35              40              45

Ser Ile Ser Glu Thr Asn Met Asp Phe Thr Met Thr Phe Tyr Leu Arg
    50              55              60

His Tyr Trp Lys Asp Glu Arg Leu Ser Phe Pro Ser Thr Ala Asn Lys
65              70              75              80

Ser Met Thr Phe Asp His Arg Leu Thr Arg Lys Ile Trp Val Pro Asp
            85              90              95

Ile Phe Phe Val His Ser Lys Arg Ser Phe Ile His Asp Thr Thr Met
            100             105             110

Glu Asn Ile Met Leu Arg Val His Pro Asp Gly Asn Val Leu Leu Ser
        115             120             125

Leu Arg Cys Leu Gln
        130
```